United States Patent [19]
Riddick et al.

[11] Patent Number: 5,886,047
[45] Date of Patent: Mar. 23, 1999

[54] TOPICAL PHARMACEUTICAL PREPARATION FOR FEVER BLISTERS AND OTHER VIRAL INFECTIONS AND METHOD OF USE

[76] Inventors: Kenneth B. Riddick, 918 Liberty St.; Joe G. Matheson, Jr., 419 Mitchell St.; Louis E. Mizelle, Jr., Rte. 2, Box 175, all of Ahoskie, N.C. 27910

[21] Appl. No.: 163,155

[22] Filed: Dec. 6, 1993

Related U.S. Application Data

[63] Continuation of Ser. No. 846,734, Mar. 5, 1992, Pat. No. 5,331,012, which is a continuation of Ser. No. 559,617, Jul. 30, 1990, abandoned.

[51] Int. Cl.$^6$ .................. A61K 31/16; A61K 31/125
[52] U.S. Cl. ............................. 514/626; 514/692
[58] Field of Search ...................... 514/626, 692

[56] References Cited

U.S. PATENT DOCUMENTS 3,136,691  6/1964  Nordstrom et al. ............... 167/52
4,628,063  12/1986  Haines et al. ..................... 514/626

OTHER PUBLICATIONS

Remington's Pharmaceutical Sciences 17$^{th}$ ed 1985 p. 1165.

Finnerty 107 CA:161701x 1987.

Richards 73 CA:42611n 1970.

*Primary Examiner*—Russell Travers
*Attorney, Agent, or Firm*—Jenkins & Wilson, P.A.

[57] ABSTRACT

The present invention relates to a method and pharmaceutical composition for treating fever blisters or cold sores in mammals, and particularly in humans, by topically administering a pharmaceutical composition comprising ethyl alcohol in a concentration of at least 85% W/V and lidocaine in a concentration of 0.5–10% W/V at a periodicity of at least 10 to 12 times daily.

2 Claims, No Drawings

TOPICAL PHARMACEUTICAL PREPARATION FOR FEVER BLISTERS AND OTHER VIRAL INFECTIONS AND METHOD OF USE

RELATED APPLICATIONS

This is a continuation of Ser. No. 07/846,734, filed Mar. 5, 1992, and issued as U.S. Pat. No. 5,331,012 on Jul. 19, 1994, which is a continuation of application Ser. No. 07/559,617, filed Jul. 30, 1990 and now abandoned.

TECHNICAL FIELD

This invention relates to a method and pharmaceutical composition for topically treating fever blisters or cold sores and other viral infections in mammals, and in particular in humans.

BACKGROUND ART

"Fever blisters" or "cold sores" have long been a very unpleasant manifestation of viral Herpes-type infections. Typically, the lesions form on the lips and/or genital area of a human and are very uncomfortable as well as unsightly during the several week healing period. Since these lesions are normally of a recurring nature, a remedy which will serve to relieve the discomfort and expedite the healing process has long been sought after.

In an effort to address the discomfort of fever blisters, cold sores and other lesions caused by Herpes-type viruses, many home remedies have been used over the years without any significant success. Also, commercial products have been developed in recent years to attempt to treat the viral infections. Representative of such products are the following: CAMPHO-PHENIQUE manufactured by Winthrop Consumer Products of New York, N.Y.; HERPECIN-L manufactured by Campbell Labs of New York, N.Y.; and BLISTEX manufactured by Blistex Incorporated of Oakbrook, Ill. Unfortunately, none of the commercial formulations have been found to be entirely satisfactory when used as topical preparations for treating humans for fever blisters or cold sores and other viral infections of both the single occurrence as well as recurrent type.

Of interest, U.S. Pat. No. 4,628,063 to Haines et al. discloses that the use of lidocaine, and particularly lidocaine in combination with a pantothenic acid, is an effective anti-viral agent in use to treat Herpes virus infections in mammals and is particularly effective in the treatment of HSV oral and genital lesions on humans. Haynes et al. discloses that lidocaine, a local anesthetic agent, and pantothenic acid (Vitamin B5) have an anti-viral effect on mammals, including human beings. It is further disclosed that lidocaine administered in the form of a pharmaceutical formulation comprising lidocaine and pantothenic acid together with a pharmaceutically acceptable carrier is particularly effective when injected in a single daily dosage or topically applied in an ointment or solution form 3 to 4 times daily. Unfortunately, this formulation is not entirely satisfactory due to the inconvenience of injections and the lengthy time of therapy required for topical treatment.

DISCLOSURE OF THE INVENTION

In accordance with the present invention, applicants provide a pharmaceutical composition for topically treating fever blisters or cold sores, Herpes virus infections, and other viral infections in mammals, and particularly in humans. The pharmaceutical composition comprises ethyl alcohol in a concentration of at least 85% W/V and lidocaine or a pharmaceutically acceptable salt thereof in a concentration of 0.5 to 10% W/V, preferably about 1–2% W/V. Optionally, the formulation may also include camphor in a concentration of 0.5 to 5% W/V, and preferably about 1.5% W/V. In use, the pharmaceutical composition is topically applied to the infected area in an effective anti-viral amount at least 10 to 12 times daily until the lesions heal.

It is therefore the object of this invention to provide an improved pharmaceutical composition for topically treating fever blisters or cold blisters on mammals.

It is another object of the present invention to provide a pharmaceutical composition for topically treating fever blisters or cold blisters, Herpes virus infections, and other viral infections which manifest themselves in a sore or lesion on the human body.

It is yet another object of the present invention to provide a pharmaceutical composition for topically treating fever blisters or cold sores, Herpes virus infections, and other viral infections which expeditiously relieves the discomfort of the lesion and results in the healing or remission of the lesion within only several days.

It is still another object of the present invention to provide a pharmaceutical composition in a gel or liquid form for topical treatment of fever or cold blisters which results in the curing or remission thereof within 3 or 4 days when applied directly to the lesion at least 10 to 12 times daily.

Some of the objects of the invention having been stated, other objects will become evident as the description of the invention proceeds.

BEST MODE FOR CARRYING OUT THE INVENTION

Applicants have discovered that ethyl alcohol (typically 95% V/V, although other concentrations may be used, and all concentrations hereinafter being referred to as "ethyl alcohol") is an effective anti-viral agent for use in treating fever blisters or cold sores and other Herpes-type virus infections on mammals, and in particular on humans, when applied directly to the lesions at least 10 to 12 times daily. Furthermore, applicants have discovered that the addition of lidocaine or a pharmaceutically acceptable salt thereof to the ethyl alcohol significantly enhances the effectiveness of the drug. Optionally, camphor may also be added to the formulation.

Applicants are believed to be the first to discover that ethyl alcohol can very successfully treat fever blisters or cold sores on humans when applied directly to the lesions at least 10 to 12 times daily, and preferably 2 to 3 times per hour during the first day of application of the formulation. Although applicants believe the ethyl alcohol to be effective without the addition of other agents to treat fever blisters or cold sores, the preferred formulation also includes lidocaine. Lidocaine (2-diethylaminoacetyl-2 6-xylidide) is known for its properties as a topical local anesthetic and serves to reduce the pain associated with the fever blister or cold sore lesions while the ethyl alcohol acts to cause the lesions to heal or go into remission. Also, camphor may be added to the formulation and is an enhancement thereto due to its known properties as a counter-irritant.

While a pharmaceutical formulation in accordance with the present invention can vary, applicants presently contemplate that the formulation will comprise at least 85% W/V (by weight per unit volume) of ethyl alcohol, and lidocaine or a pharmaceutically acceptable salt thereof in a concentration of 0.5 to 10% W/V, and preferably about 1–2% W/V.

Optionally, a concentration of 0.5 to 5% W/V, preferably about 1.5% W/V, of camphor may be added to the pharmaceutical formulation to enhance its counter-irritant characteristics.

LABORATORY EXAMPLES

Although many formulations are possible of the pharmaceutical composition contemplated by the applicants, three preferred formulations are set forth below. As noted above, 95% V/V ethyl alcohol was used in making these formulations. All formulations are for 100 ml of topical treatment composition, and the weight per unit volume (W/V) of each component thereof is as follows:

| Formulation 1 | |
| --- | --- |
| Ethyl Alcohol | 97.5% W/V of 95% V/V Ethyl Alcohol |
| Lidocaine | 1.0% W/V |
| Camphor | 1.5% W/V |
| Total | 100 ml |

| Formulation 2 | |
| --- | --- |
| Ethyl Alcohol | 99.0% W/V of 95% V/V Ethyl Alcohol |
| Lidocaine | 1.0% W/V |
| Total | 100 ml |

| Formulation 3 | |
| --- | --- |
| Ethyl Alcohol | 87.5% W/V of 95% V/V Ethyl Alcohol |
| Lidocaine | 1.0% W/V |
| Camphor | 1.5% W/V |
| Methylcellulose | 10.0% W/V |
| Total | 100 ml |

As will be noted above, Formulation 3 contains a thickening agent, methylcellulose, in order to render the pharmaceutical composition more gel-like than the liquid solutions of Formulations 1 and 2. As a matter of choice, the pharmaceutical formulation may be a liquid solution or, if desired, 5–15% W/V of a suitable thickening agent (such as methylcellulose) may be added to render the composition more gel-like. Whether the pharmaceutical composition of the invention is in liquid or gel form is a matter of choice, and the use of a thickening agent is conventional and known to those skilled in the art.

In use, the topical pharmaceutical formulation of the invention should be applied directly to the fever blister or cold sore lesion at least 10 to 12 times daily, and applications as often as every 20 minutes have yielded very good results with no reported adverse side effects. Normally topical application of the formulation should begin at the first signs of a lesion and continue at the rate of 1 to 3 applications per hour during waking hours until the lesion is completely eradicated. Although therapy should begin as early as possible, applicants have found that topical treatment of fully erupted fever blisters results in enhanced healing and thus believe that the formulation is effective when applied at any stage of lesion development.

After extensive testing on human subjects with varying types of viral lesions, applicants have found the pharmaceutical formulation of the invention to provide unexpected and surprisingly effective results in reducing pain and facilitating healing of lesions. Although intended primarily for fever blisters or cold sores, applicants have found the pharmaceutical formulation to be effective with Herpes virus infections and believe that the formulation would also be effective in healing lesions from other related viral-type infections.

Applicants have treated a number of human subjects with the pharmaceutical formulation and had surprisingly successful results in over 90% of the cases. In the study, the patients were initially seen at varying times after the appearance of fever blisters or cold sores and were advised to apply the pharmaceutical treatment of the invention directly to the lesion as often as possible in the morning, in the afternoon, and at night before going to bed. The results of the human case studies indicate that the pharmaceutical formulation, topically applied to lesions, is able to successfully treat fever blisters or cold sores and other viral infections in humans. Representative case studies are set forth below:

Human Case Studies

EXAMPLE 1

A 68 year old male started treatment with Formulation 1 at the first signs of an oral fever blister. The formulation was applied topically about 6 to 7 times per day and resulted in a complete remission of the lesion in 3 days.

EXAMPLE 2

A 38 year old male had Herpes Genitalis lesions on his penis. The pharmaceutical formulation (Formulation 2) was applied directly to the lesions 5 times daily, and complete remission was achieved in 4 days.

EXAMPLE 3

A 34 year old female who frequently experienced oral fever blisters was using a prescription formulation sold under the tradename ACYCLOVIR. The patient applied the pharmaceutical formulation of the invention (Formulation 1) as directed and reported complete remission of the lesions.

EXAMPLE 4

A 34 year old male had multiple lesions around the mouth wherein one or two of the lesions were fully erupted. The pharmaceutical formulation of the invention (Formulation 2) was applied as directed. At the end of day 1 the patient reported considerable comfort improvement, and at the end of day 3 a complete remission occurred.

EXAMPLE 5

A 55 year old female had two to three day old oral lesions. The pharmaceutical formulation (Formulation 1) was applied as directed, and complete remission occurred in two to three days.

EXAMPLE 6

A 60 year old male had chronic lesions and cracking of his lips for a period of 1 year, and his lips were reported to crack and bleed periodically. The pharmaceutical formulation (Formulation 2) was applied several times daily and relief was felt within several days and complete healing occurred in 30 days. Due to the severity of the case, the patient experienced burning from the ethyl alcohol in the formulation, but he continued to use the formulation with no adverse side effects and reported the formulation to be excellent.

EXAMPLE 7

An 84 year old male had Herpes Zoster ("shingles") condition for several months. The pharmaceutical formulation (Formulation 2) was applied 12–15 times daily, and the patient reported that the burning had stopped and the soreness and pain had been relieved over a period of 2.5 days.

The patient reported spending about $800.00 in the previous months in an unsuccessful effort to obtain relief for his condition.

It will be understood that various details of the invention may be changed without departing from the scope of the invention. Furthermore, the foregoing description is for the purpose of illustration only, and not for the purpose of limitation—the invention being defined by the claims.

What is claimed is:

1. A pharmaceutical composition for topically treating fever blisters and Herpes virus infections in mammals in need of such treatment consisting essentially of:

95% V/V ethyl alcohol in a concentration of about 97.5% to about 99.0% W/V; and lidocaine or a pharmaceutically acceptable salt thereof in a concentration of about 1.0% to about 2.5% W/V.

2. A method of treating fever blisters and Herpes virus infections in mammals in need of such treatment, which consists essentially of topically applying to the infected area an effective anti-viral amount of a mixture consisting essentially of:

95% V/V ethyl alcohol in a concentration of about 97.5% to about 99.0% W/V; and lidocaine or a pharmaceutically acceptable salt thereof in a concentration of about 1.0% to about 2.5% W/V.

* * * * *